(12) United States Patent
Stoll

(10) Patent No.: US 6,610,324 B2
(45) Date of Patent: *Aug. 26, 2003

(54) FLUPIRTINE IN THE TREATMENT OF FIBROMYALGIA AND RELATED CONDITIONS

(75) Inventor: Andrew L. Stoll, Lincoln, MA (US)

(73) Assignee: The McLean Hospital Corporation, Belmont, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/534,325

(22) Filed: Mar. 24, 2000

(65) Prior Publication Data

US 2002/0018809 A1 Feb. 14, 2002

Related U.S. Application Data

(60) Provisional application No. 60/128,141, filed on Apr. 7, 1999, now abandoned.

(51) Int. Cl.$^7$ ............................. A61K 9/20; A61K 9/14; A61L 9/04; A61F 13/00
(52) U.S. Cl. ........................ 424/464; 424/45; 424/489; 424/434
(58) Field of Search ......................... 424/464, 45, 489, 424/434

(56) References Cited

U.S. PATENT DOCUMENTS

| | | | | |
|---|---|---|---|---|
| 5,162,346 A | * | 11/1992 | Lobish et al. | 514/356 |
| 5,252,333 A | | 10/1993 | Horrobin | 424/422 |
| 5,707,642 A | * | 1/1998 | Yue | 424/423 |

FOREIGN PATENT DOCUMENTS

| | | | | |
|---|---|---|---|---|
| EP | 289 204 | | 11/1998 | A61K/31/20 |
| WO | 94/28913 | | 12/1994 | A61K/37/00 |

OTHER PUBLICATIONS

Bennett, et al. "Intravenous Lignocaine in the Management of Primary Fibromyalgia Syndrome," *Intl. J. Clin. Pharm. Res.* 15:115–119 (1995).
Carette, et al., "Comparison of Amitriptyline, Cyclobenzaprine, and Placebo in the Treatment of Fibromyalgia," *Arthritis Rheum.* 37:32–40 (1994).
Drewes, et al., "Zopiclone in the Treatment of Sleep Abnormalities in Fibromyalgia," *Scand. J. Rheumatol.* 20:288–293 (1991).
Goldenberg, et al., "A Randomized, Controlled Trial of Amitriptyline and Naproxen in the Treatment of Patients with Fibromyalgia," *Arthritis Rheum.* 29:1371–1377 (1986).
Hrycaj, et al., "Pathogenetic Aspects of Responsiveness to Ondansetron (5–Hydroxytryptamine Type 3 Receptor Antagonist) in Patients with Primary Fibromyalgia Syndrome—A Preliminary Study," *J. Rheumatol.* 23:1418–1423 (1996).

Fossaluza, et al., "Combined Therapy with Cyclobenzaprine and Ibuprofen in Primary Fibromyalgia Syndrome," *Int. J. Clin. Pharm. Res.*, 12:99–102 (1992).
Johnson, "Fluoxetine and Amitriptyline in the Treatment of Fibromyalgia," *J. Fam. Pract.* 44:128–130 (1997).
Moldofsky, "The Effect of Zolpidem in Patients with Fibromyalgia: A Dose Ranging, Double Blind, Placebo Controlled, Modified Crossover Study," *J. Rheumatol.* 23:529–533 (1996).
Oye, et al., "Analgetisk Effekt av Ketamin hos en Pasient Med Neuropatiske Smerter," *Tidsskr Nor Laegeforen* 26:3130–3131 (1996).
Vaeroy, et al., "Treatment of Fibromyalgia (Fibrositis Syndrome): A Parallel Double Blind Trial with Carisoprodol, Paracetamol and Caffeine (Somadril Comp) Versus Placebo," *Clin. Rheumatol.* 8:245–250 (1989).
Yunus, et al., "Short Term Effects of Ibuprofen in Primary Fibromyalgia Syndrome: A Double Blind, Placebo Controlled Trial," *J. Rheumatol.* 16:527–532 (1989).
Worz, "Flupirtine in the treatment of Chronic Myofascial Pain," *Fortschr. Med.* 109:68–70 (1991).*
Herrman, "Long Term Tolerance of Flupirtine. Open Multicenter Study Over One Year," *Fortschr. Med.* 111:266–770 (1993).*
Friedel, "Flupirtine. A Review of its Pharmacological Properties, and Therapeutic Efficacy in Pain State," *Drugs* 4:548–69 (1993).*
Herrman, "On the adverse reactions of efficacy of long–term treatment with flupirtine," *Postgrad Med J* 63: 87–103 (1987).*
Worz, "Flupirtine in comparison with chlormezanone in chronic musculoskeletal back pain," *Fortschr. Med.* 114:46–50 (1996).*
Scheef, "Flupirtine in patients with cancer pain," *Arzneimittelforschung* 35: 75–7 (1985) Abstract.*
Brückle, et al., "Treatment of Fibromyalgia Syndrome," *Akt. Rheumatol.* 20: 13–19 (1995), (translation).
Goldenberg, "Fibromyalgia, Chronic Fatigue, and Myofascial Pain Syndromes," *Current Opinion in Rheumatology* 4:3247–257 (1992), (translation).
Stoll, "Fibromyalgia Symptoms Relieved by Flupirtine: An Open–Label Case Series," *Psychosomatics* 41:372 (2000) (translation).
Worz, "Studies on Myalgias and Insertion Tendomyopathy," *Munchener Medizinische Wochenschrift* 132/47Supp.(9) (1990), translation).
Worz, "Flupirtine in the Treatment of Chronic Myofascial Pain," *Fortschr. Med.* 109:68–70 (1991), (translation).
Worz, et al., "Flupirtine in Comparison with Chlormezanone in Chronic Musculoskeletal Back Pain," *Fortschr. Med* 114:46–50 (1996), (translation).

* cited by examiner

*Primary Examiner*—Thurman K. Page
*Assistant Examiner*—Rachel M. Bennett
(74) *Attorney, Agent, or Firm*—Michael A. Sanzo; Fitch, Even, Tabin & Flannery

(57) ABSTRACT

The present invention is directed to a method for treating the symptoms associated with fibromyalgia and related conditions by administering flupirtine.

7 Claims, No Drawings

FLUPIRTINE IN THE TREATMENT OF FIBROMYALGIA AND RELATED CONDITIONS

CROSS-REFERENCE TO RELATED APPLICATIONS

The present application claims the benefit of U.S. provisional application No. 60/128,141, filed on Apr. 7, 1999 (now abandoned).

FIELD OF THE INVENTION

The present invention is directed to medical treatments for fibromyalgia and related conditions. Specifically, the invention is directed to the administration of the drug flupirtine as a means for alleviating the symptoms associated with these disorders.

BACKGROUND OF THE INVENTION

Fibromyalgia is a chronic condition characterized by pain in muscles, fascia and joints. Other symptoms typically include sleep disturbances, chronic fatigue and major depression. The etiology and pathophysiology of fibromyalgia are unknown, but it is clear that the central nervous system is involved. Patients may obtain a degree of relief from analgesic drugs, antidepressants and adjunctive treatments such as moderate exercise, proper diet and stress reduction techniques. Table 1 summarizes the studies that have been carried out in an effort to find an effective drug treatment.

TABLE 1

Drug Treatments for Fibromyalgia

| Treatment | Drug Class* | Study Method** | Efficacy | Reference |
|---|---|---|---|---|
| fluoxetine | 1 | open | + | Johnson, J. Fam. Pract., 44: 128–30 (1997) |
| fluoxetine | 1 | open | + | Finestone, et al., J.A.M.A., 264: 2869–70 (1990) |
| fluoxetine | 1 | open | + | Goldenberg, et al., Arthritis Rheumatol., 39: 1852–9 (1996) |
| fluoxetine | 1 | db | ± | Wolfe, et al., Scand. J. Rheumatol., 23: 255–9 (1994) |
| fluoxetine | 1 | open | − | Cortet, et al., Rev. Rheum. Mal. Osteoartic, 59: 497–500 (1992) |
| citalopram | 1 | db | − | Norregaard, et al., Pain, 61: 445–9 (1995) |
| amitriptyline | 1 | db | + | Carette, et al., Arthritis Rheum., 37: 32–40 (1994) |
| amitriptyline | 1 | db | + | Carette, et al., Arthritis Rheumatol., 29: 655–9 (1986) |
| amitriptyline | 1 | db | + | Goldenberg, et al., Arthritis Rheum., 39: 1852–9 (1996) |
| amitripthline | 1 | db | + | Goldenberg, et al., Arthritis Rheum., 29: 1371–7 (1986) |
| amitriptyline | 1 | db | + | Jaeschke, et al., J. Rheumatol., 18: 447–51 (1991) |
| amitriptyline | 1 | db | + | Scudds, et al., J. Rheumatol., 16: 98–103 (1989) |
| fluphenazine plus amitriptyline | 7, 1 | open | + | Connolly, Del. Med. J., 53: 189–91 (1981) |
| naproxen plus amitriptyline | 1, 2 | db | + | Goldenberg, et al., Arthritis Rheum., 29: 1371–7 (1986) |
| ondansetron | 9 | db | + | Hrycaj, et al., J. Rheumatol., 23: 1418–23 (1996) |
| tropisetron | 9 | open | + | Samborski, et al., Mater Med. Pol., 28: 17–9 (1996) |
| katenserin | 9 | open | + | Stratz, et al., Z. Rheumatol., 50: 21–2 (1991) |
| lithium carbonate | 6 | open | | Teasell, Can. Med. Assoc. J., 144: 122–3 (1991) |
| lithium carbonate | 6 | open | | Tyber, Can., Med Assoc. J., 143: 902–4 (1990) |
| fluoxetine plus cyclobenzaprine | 1, 3 | open | + | Cantini, et al., Minerva Med., 85: 97–100 (1994) |
| cyclobenzaprine | 3 | db | + | Carette, et al., Arthritis Rheum., 37: 32–40 (1994) |
| cyclobenzaprine | 3 | db | + | Bennett, Arthritis Rheum., 31: 1535–42 (1988) |
| cyclobenzaprine | d | db | + | Quimby, et al., J. Rheumatol Suppl., 19: 140–3 (1989) |
| low-dose hs cyclobenzaprine | 3 | db | + | Santandrea, et al., J. Int. Med. Res., 21: 74–80 (1993) |
| cyclobenzaprine plus ibuprofen | 3, 2 | open | + | Fossaluzza, et al., Int. J. Clin. Pharmacol. Res., 12: 99–102 (1992) |
| carisoprodol plus acetaminophen plus | 3, 12, 13 | db | + | Vaeroy, et al., Clin. Rheumatol., 8: 245–50 (1989) |

TABLE 1-continued

Drug Treatments for Fibromyalgia

| Treatment | Drug Class* | Study Method** | Efficacy | Reference |
|---|---|---|---|---|
| caffeine Zolpidem | 4 | db | ± | Moldofsky, et al., J. Rheumatol., 23: 529–33 (1996) |
| ibuprofen plus alprazolam | 4 | db | ± | Russell, et al., Arthritis Rheum., 34: 552–60 (1991) |
| ketamine | 15 | open | ± | Oye, et al., Tidsskr. Nor. Laegeforen, 116: 3130–1 (1996) |
| indomethacin | 2 | open | + | Kelly, J. Am. Geriatr. Soc., 14: 48–55 (1996) |
| naproxen | 2 | db | ± | Goldenberg, et al., Arthritis Rheum., 29: 1371–7 (1986) |
| tenoxicam | 2 | db | + | Schorn, S. Afr. Med. J., 69: 301–3 (1986) |
| ibuproxam | 2 | open | + | Ferri, et al., Minerva Med., 74: 331–6 (1983) |
| tolmetin | 2 | db | + | Balme, et al., Curr. Med. Res. Opin, 7: 127–30 (1980) |
| tiaprofenic acid | 2 | db | + | Donald, et al., J. Int. Med. Res., 8: 382–7 (1980) |
| aspirin | 2 | db | + | Donald, et al., J. Int. Med. Res., 8: 832–7 (1980) |
| ibuprofen | 2 | db | + | Le Gallez, et al., Curr. Med. Res. Opin., 10: 663–7 (1988) |
| ibuprofen | 2 | db | − | Yunus, et al., J. Rheumatol., 16:527–32 (1989) |
| ibuprofen plus meptazinol | 2, 9 | db | + | Le Gallez, et al., Curr. Med. Res. Opin., 10: 663–7 (1998) |
| phenylbutazone | 2 | db | + | Balme, et al., Curr. Med. Res. Opin., 7: 127–30 (1980) |
| phenylbutazone plus prednisone | 2, 8 | open | | Settel, Curr. Ther. Res. Clin. Exp., 9: 197–9 (1967) |
| topical capsaicin | 10 | open | + | Mathias, et al., Am. J. Phys. Med. Rehabil., 74: 39–44 (1995) |
| local trigger point injections | 11 | open | ± | Hong, et al., Arch. Phys. Med. Rehabil., 77: 1161–6 (1996) |
| local trigger point injections | 11 | open | | Jayson, Bull. Hosp. Jt. Dis., 55: 176–7 (1996) |
| antibiotics specific for Lyme disease | 5 | open | − | Dinerman, et al., Ann. Inter. Med., 117: 281–5 (1992) |
| prednisone | 8 | db | − | Clark, et al., J. Rheumatol., 12: 980–3 (1985) |
| chlormezanone | 16 | db | − | Pattrick, et al., Br. J. Rheumatol., 32: 55–8 (1993) |
| proglumetacin | 16 | open | + | Gusso, et al., Minerva Med., 76: 567–73 (1985) |
| acetaminophen | 12 | db | − | Hrycaj, et al., J. Rheumatol., 23: 1418–23 (1996) |
| s-adenosyl-methionine | 16 | db | + | Jacobsen, et al., Scand. J. Rheumatol., 20: 294–302 (1991) |
| zopiclone | 16 | db | ± | Drewes, et al., Scand. J. Rheumatol., 20: 288–93 (1991) |
| zopiclone | 16 | db | − | Gronblad, et al., Clin. Rheumatol., 12: 186–91 (1993) |
| intravenous lignocaine | 14 | open | + | Bennett, et al., Int. J. Clin. Pharmacol. Res., 15: 115–9 (1995) |
| 5-OH-L-tryptophan | 16 | open | + | Puttini, et al., J. Int. Med. Res. 20: 182–9 (1992) |
| malic acid + magnesium | 16, 16 | db | + | Russell, et al., J. Rheumatol., 22: 953–8 (1995) |
| tamoxifen | 16 | open | | Simonson, Lakartidningen, 93: 340 (1996) |
| botulinum toxin | 16 | open | − | Paulson, et al., Mov. Disord., 11: 459 (1996) |

*Drug class key: 1 = antidepressant; 2 = NSAIDs; 3 = muscle relaxants (nonbenzodiazepine); 4 = benzodiazepine; 5 = antibiotics; 6 = mood stabilizer; 7 = antipsychotic agent; 8 = corticosteroid; 9 = serotonin (2 or 3) receptor antagonist; 10 = topical agents; 11 = trigger point injection; 12 = acetaminophen; 13 = caffeine; 14 = intravenous anesthetics; 15 = NMDA (glutamate) receptor ligand; 16 = miscellaneous agents.
**Study method: db = double-blind Despite the efforts that have been made, there is still no treatment that is effective in the majority of patients with fibromyalgia. Thus, there is a clear need for new therapies designed to alleviate the suffering of patients with this, and closely related, conditions.

SUMMARY OF THE INVENTION

Flupirtine is an analgesic that has been used in Europe to treat the pain associated with surgery, cancer, trauma, and liver disease. It acts via the central nervous system through non-opite pain pathways, possibly involving the thalamus or spinal pain pathways. In some, but not all, studies flupirtine has been found to be as effective as opiates in relieving pain. Moreover, flupirtine offers a clear advantage over opiates in that it is not addictive and there have been no reports of abuse. The present invention is based upon the unexpected discovery that flupirtine is capable of completely eliminating the chronic and severe body pain present in some patients with fibromyalgia. Relief is possible even when high doses of opiates, non-steroidal anti-inflammatory drugs and placquenil fail to alleviate pain.

In its first aspect, the invention is directed to a method of treating a patient with fibromyalgia by administering a pharmaceutical composition containing flupirtine. The dosage of flupirtine should be sufficient to reduce or eliminate one or more of the symptoms that have been associated with fibromyalgia. These symptoms include diffuse musculoskeletal pain, fatigue, ocular and vestibular disturbances, headaches, paresthesias, esophageal dysmotility, sleep disturbances, and severe depression. The flupirtine may be administered in any dosage form including tablets, capsules, gels, or topical preparations and should be given at a daily dosage of between 50 and 900 mg, calculated on the basis of the free base form of the drug. In general, dosage should not exceed 600 mg per day and the optimal range should typically be between 100 and 400 mg per day. The flupirtine may be administered in either a single or, preferably, multidosage daily regimen.

In addition, the present invention is directed to methods of treating a patient for diseases or conditions that are related to fibromyalgia by administering flupirtine. Again, the dosage should be between 50 and 900 mg per day, calculated on the basis of the free base form of the drug, and should preferably be between 100 and 400 mg per day. The flupirtine may be given in any dosage form and administration may be accomplished by any route. Specific diseases that are defined as being related to fibromyalgia include fibrositis; chronic fatigue syndrome; myofascial pain syndrome, soft tissue rheumatism; idiopathic muscle pain syndrome; chronic widespread musculoskeletal pain; major depression associated with musculoskeletal pain; somatization disorder; somatoform pain disorder; Lyme disease with concurrent fibromyalgia; rheumatoid arthritis with concurrent fibromyalgia; generalized tendomyopathy; eosinophilia-myalgia syndrome; and stiff-man syndrome.

DETAILED DESCRIPTION OF THE INVENTION

Fibromyalgia is one of the most common conditions seen by rheumatologists. Strict criteria for the diagnosis and classification of fibromyalgia have been established by, inter alia, the American College of Rheumatology. The main clinical characteristic is generalized pain and widespread tenderness on palpation in specific areas of the musculoskeletal system. Stiffness, chronic fatigue and a specific sleep disturbance are also commonly present along with a number of other symptoms. The condition may be either idiopathic (primary fibromyalgia) or it may be associated with other underlying conditions such as ankylosing spondylitis, trauma or surgery (secondary fibromyalgia).

Flupirtine, a triaminopyridine compound with antinociceptive effects, has been marketed in Europe for several years by Asta Medica under the brand name Katadolon™. Although it has been used as an analgesic for cancer pain, post-operative pain, dental pain, degenerative rheumatic arthrosis, and inflammatory rheumatoid arthritis, it has not previously been known to be useful as a treatment for fibromyalgia. The present invention is based upon the discovery that flupirtine is unexpectedly effective in alleviating symptoms of fibromyalgia.

Chemical Form of Flupirtine

The present invention is not limited to any particular chemical form of flupirtine and the drug may be given to patients either as a free base or as a pharmaceutically acceptable acid addition salt. In the latter case, the hydrochloride salt is generally preferred but other salts derived from organic or inorganic acids may be also used. Examples of such acids include, without limitation, hydrobromic acid, phosphoric acid, sulfuric acid, methane sulfonic acid, phosphorous acid, nitric acid, perchloric acid, acetic acid, tartaric acid, lactic acid, succinic acid, citric acid, malic acid, maleic acid, aconitic acid, salicylic acid, thalic acid, embonic acid, enanthic acid, and the like. The preparation of flupirtine, 2-amino-3-carbethoxyamino-6-(4-fluorobenzylamino)-pyridine, and its physiologically acceptable salts is described in German patents 1,795,858 and 3,133,519.

Dosage

The total daily dosage of flupirtine administered to a patient should be at least the amount required to reduce or eliminate one or more of the symptoms associated with fibromyalgia, preferably musculoskeletal pain. The typical daily dosage will be between 100 and 300 mg and, in general, the daily dosage should not exceed 600 mg. Higher doses may be tolerated by some patients and daily dosages of 1,000 mg or more may be considered in refractory cases or in patients receiving concomitant drug treatment with agents that may lower the serum concentration and half-life of flupirtine (e.g., cytochrome P450 inducing compounds such as carbamazetine, phenytoin, phenobarbital and rifampin) as well as in cigarette smokers. In contrast, elderly patients, patients with renal or hepatic dysfunction, and patients receiving concomitant drugs which inhibit the cytochrome P450 system should receive lower initial and maintenance doses, e.g., 75 mg. These dosages are simply guidelines and the actual dose selected for an individual patient will be determined by the attending physician based upon clinical conditions and using methods well-known in the art. Flupirtine may be provided in either a single or multiple dosage regimen, e.g., a patient may take 100 mg of flupirtine orally three times a day.

Dosage Forms and Route of Administration

Any route of administration and dosage form is compatible with the present invention and flupirtine may be administered as either the sole active agent or in combination with other therapeutically active drugs. Although compositions suitable for oral delivery are preferred, other routes that may be used include peroral, internal, pulmonary, rectal, nasal, vaginal, lingual, transdermal, intravenous, intraarterial, intramuscular, intraperitoneal, intracutaneous and subcutaneous routes. Specific dosage forms include tablets, pills, capsules, powders, aerosols, suppositories, skin patches, parenterals, and oral liquids including oil aqueous suspensions, solutions and emulsions. Sustained release dosage forms may also be used. All dosage forms may be prepared using methods that are standard in the art (see e.g., *Remington's Pharmaceutical Sciences*, 16th ed., A. Oslo Editor, Easton Pa. (1980)). Specific guidance for the preparation of dosage forms for various routes of delivery is provided by U.S. Pat. Nos. 4,668,684; 5,503,845; and 5,284,861.

Flupirtine may be used in conjunction with any of the vehicles and excipients commonly employed in pharmaceutical preparations, e.g., talc, gum arabic, lactose, starch, magnesium stearate cocoa butter, aqueous or non-aqueous solvents, oils, paraffin derivatives, glycols, etc. Coloring and flavoring agents may also be added to preparations, particularly to those for oral administration. Solutions can be prepared using water or physiological compatible organic solvents such as ethanol, 1,2-propylene glycol, polyglycols, dimethyl sulfoxide, fatty alcohols, triglycerides, partial esters of glycerine and the like. Parenteral compositions containing flupirtine may be prepared using conventional techniques and include sterile isotonic saline, water, 1,3-butanediol, ethanol, 1,2-propylene glycol, polyglycols mixed with water, Ringer's solution, etc.

Method of Treatment

Generally, a patient diagnosed as having fibromyalgia may be initially given a relatively low dose of flupirtine, e.g., 50 mg per day, in order to determine whether any adverse side-effects are experienced. This is particularly important in cases where a patient is taking other medications or has clinical characteristics that suggest that they may not be able to tolerate high drug dosages. Although flupirtine is relatively safe when used at dosages lower than 600 mg per day, a number of side effects have been reported. Among these are dizziness, drowsiness, pruritus, dry mouth, and, less frequently, nausea, depression, sleep disturbance, and headache. If adverse effects are not experienced by the patient, dosage may be gradually increased until a satisfactory alleviation of the symptoms associated with fibromyalgia, particularly pain, is achieved. Since flupirtine is non-addictive, treatment may be safely maintained over a prolonged period of time.

The daily dose of flupirtine may be administered as a single tablet or capsule, but it is generally preferable to divide the daily dosage into two or more separate aliquots. Alternatively, a patient may simply take flupirtine as needed, up to the maximum tolerated daily dosage. Flupirtine administration may be combined with the administration of other therapeutically active agents, such as antidepressants, depending upon the individual needs of a patient.

Treatment of Diseases or Conditions Related to Fibromyalgia

In addition its use in the treatment of fibromyalgia, flupirtine may be used in exactly the manner described above for the treatment of a number of diseases and conditions related to fibromyalgia. Included among such diseases and conditions are fibrositis, chronic fatigue syndrome, myofascial pain syndrome, soft tissue rheumatism, non-articular rheumatism, idiopathic muscle pain syndrome, chronic widespread musculoskeletal pain, major depression associated with musculoskeletal pain, somatization disorder, somatoform pain disorder, Lyme disease with concurrent fibromyalgia, rheumatoid arthritis with concurrent fibromyalgia, generalized tendomyopathy, eosinophilia-myalgia syndrome, and stiff-man syndrome.

Advantages of Flupirtine Over Opiates

Patients receiving flupirtine do not acquire a tolerance to its analgesic effects the way that patients receiving opiates do. Thus, there is no need for a continual increase in dosage once an optimum has been found. Flupirtine is non-addictive and the abrupt discontinuation of its administration does not produce withdrawal symptoms. In addition, flupirtine is less sedating than opiate drugs and, unlike opiates, it exhibits muscle relaxant properties and is not associated with cardiovascular side effects.

Despite these differences in adverse effects, flupirtine has an analgesic action in patients with fibromyalgia and related conditions that is roughly comparable to the effect produced by opiates, and, in some instances, flupirtine may be superior. Thus, flupirtine has a therapeutic utility comparable to, or better than, some of the most effective antinociceptive agents known without comparable risks and side effects.

All references cited herein are fully incorporated by reference. Having now fully described the invention, it will be understood by those of skill in the art that the invention may be performed within a wide and equivalent range of conditions, parameters and the like, without affecting the spirit or scope of the invention or embodiment thereof.

What is claimed is:

1. A method of treating a patient for fibromyalgia which comprises: administering an amount of flupirtine to said patient effective to reduce or eliminate one or more of the following symptoms: chronic musculoskeletal pain; sleep disturbance; chronic fatigue; or major depression.

2. The method of claim 1, wherein said flupirtine is administered orally at a dose of between 50 mg and 900 mg per day, calculated on the basis of the free-base form of flurpirtin.

3. The method of claim 2, wherein said flupirtine is administered at a dose of between 100 mg and 400 mg per day, calculated on the basis of the free-base form of flupirtine.

4. The method of claim 1, wherein said flupirtine is administered parenterally at a dose of between 50 mg and 900 mg per day, calculated on the basis of the free-base form of flupirtine.

5. The method of claim 4, wherein said flupirtine is administered at a dosage of between 100 mg and 400 mg per day, calculated on the basis of the free-base form of flupirtine.

6. The method of claim 1, wherein said flupirtine is administered transdermally at a dosage of between 50 mg and 900 mg per day, calculated on the basis of the free-base form of flupirtine.

7. The method of claim 6, wherein said flupirtine is administered at a dosage of between 100 mg and 400 mg per day, calculated on the basis of the free-base form of flupirtine.

* * * * *